(12) United States Patent
Ouziel et al.

(10) Patent No.: US 8,007,546 B2
(45) Date of Patent: Aug. 30, 2011

(54) METHOD OF INCREASING DEPTH SHADE

(75) Inventors: Philippe Ouziel, Altkirch (FR); Ulrich Strahm, Aesch (CH)

(73) Assignee: Huntsman International LLC, The Woodlands, TX (US)

( * ) Notice: Subject to any disclaimer, the term of this patent is extended or adjusted under 35 U.S.C. 154(b) by 969 days.

(21) Appl. No.: 10/579,491

(22) PCT Filed: Nov. 10, 2004

(86) PCT No.: PCT/EP2004/052897
§ 371 (c)(1),
(2), (4) Date: May 16, 2006

(87) PCT Pub. No.: WO2005/049914
PCT Pub. Date: Jun. 2, 2005

(65) Prior Publication Data
US 2008/0178395 A1     Jul. 31, 2008

(30) Foreign Application Priority Data

Nov. 19, 2003   (EP) ..................................... 03104277

(51) Int. Cl.
*D06M 15/423*   (2006.01)
(52) U.S. Cl. ............. 8/115.6; 8/516; 106/506; 524/102; 544/212
(58) Field of Classification Search ............... 8/115.6, 8/181, 557, 490, 543, 552, 555, 549, 533; 564/473; 260/249.5, 249.8, 248, 249.6
See application file for complete search history.

(56) References Cited

U.S. PATENT DOCUMENTS

| | | | | |
|---|---|---|---|---|
| 3,963,714 A * | 6/1976 | Gerendas et al. | ............. | 544/196 |
| 4,180,664 A * | 12/1979 | Perrin et al. | ................... | 544/194 |
| 5,112,404 A | 5/1992 | Sommer et al. | ................ | 106/506 |
| 5,696,262 A | 12/1997 | Fuso et al. | ................... | 544/212 |
| 5,932,640 A | 8/1999 | Kaul et al. | ................... | 524/102 |
| 2004/0055093 A1* | 3/2004 | Offord et al. | ................ | 8/115.66 |
| 2004/0163189 A1* | 8/2004 | Bartl et al. | ....................... | 8/516 |

FOREIGN PATENT DOCUMENTS

| | | |
|---|---|---|
| DE | 39 01 717 | 7/1990 |
| DE | 101 35 941 | 2/2003 |
| EP | 0 702 011 | 3/1996 |
| WO | WO03014194 A1 * | 2/2003 |

* cited by examiner

*Primary Examiner* — Ling-Siu Choi
*Assistant Examiner* — Bijan Ahvazi

(57) ABSTRACT

The invention relates to a method of increasing the depth of shade of dyed natural or synthetic polyamide fiber materials, which comprises treating the fiber material before, during or after dyeing with a liquor comprising a compound of formula (1) wherein R is halogen, $C_1$-$C_{12}$alkyl, $C_5$-$C_{24}$aryl, $C_6$-$C_{36}$aralkyl, —$OR_1$, or —$NR_1R_2$, $R_1$ and $R_2$ being, each independently of the other, hydrogen, $C_1$-$C_{12}$alkyl unsubstituted or substituted by one or more hydroxy, amino, mercapto, carboxyl, sulfo, $C_1$-$C_{12}$alkylsulfonyl, $C_5$-$C_{24}$arylsulfonyl or $C_6$-$C_{36}$aralkylsulfonyl groups, $C_5$-$C_{24}$aryl unsubstituted or substituted by one or more hydroxy, amino, carboxyl, sulfo, $C_1$-$C_{12}$ alkylsulfonyl, $C_5$-$C_{24}$arylsulfonyl or $C_6$-$C_{36}$aralkylsulfonyl groups, or $C_6$-$C_{36}$aralkyl unsubstituted or substituted by one or more hydroxy, amino, carboxyl, sulfo, $C_1$-$C_{12}$alkylsulfonyl, $C_5$-$C_{24}$arylsulfonyl or $C_6$-$C_{36}$aralkylsulfonyl groups, X and Y are, each independently of the other, mercapto, —$NR_3R_4$ or —$N^+R_3R_4R_5A^-$, wherein $R_3$, $R_4$ and $R_5$ are, each independently of the others, hydrogen or $C_1$-$C_{12}$alkyl and $A^-$ is chloride, bromite, iodide, sulfate or methylsulfate, $R_6$ and $R_7$ are, each independently of the other, hydrogen or $C_1$-$C_{12}$alkyl, and x and y are, each independently of the other, a number from 2 to 12.

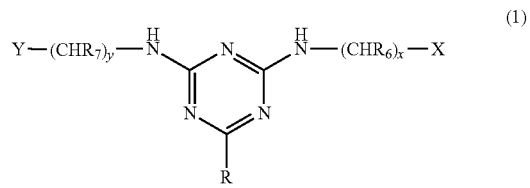

(1)

12 Claims, No Drawings

METHOD OF INCREASING DEPTH SHADE

The present invention relates to a method of increasing the depth of shade of dyed natural or synthetic polyamide fibre materials by treatment with amino-substituted triazine derivatives before, during or after dyeing.

In the dyeing of polyamide fibres, especially polyamide microfibres, dark shades can be obtained by using acid dyes, although at the expense of good fastness-to-washing properties.

Conversely, good fastness-to-washing properties are obtained when dyeing with reactive dyes, although in that case dark shades are not readily obtained.

It has now been found that dark shades having a high degree of fastness to washing can be obtained if the polyamide fibre material is treated with a liquor comprising specific amino-substituted triazines before, during or after dyeing.

The present invention relates to a method of increasing the depth of shade of dyed natural or synthetic polyamide fibre materials, which comprises treating the fibre material before, during or after dyeing with a liquor comprising a compound of formula (1)

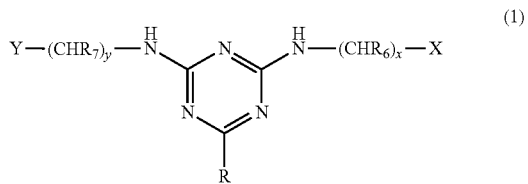

(1)

wherein R is halogen, $C_1$-$C_{12}$alkyl, $C_5$-$C_{24}$aryl, $C_6$-$C_{36}$aralkyl, —$OR_1$ or —$NR_1R_2$, $R_1$ and $R_2$ being, each independently of the other, hydrogen, $C_1$-$C_{12}$alkyl unsubstituted or substituted by one or more hydroxy, amino, mercapto, carboxyl, sulfo, $C_1$-$C_{12}$alkylsulfonyl, $C_5$-$C_{24}$arylsulfonyl or $C_6$-$C_{36}$aralkylsulfonyl groups, $C_5$-$C_{24}$aryl unsubstituted or substituted by one or more hydroxy, amino, carboxyl, sulfo, $C_1$-$C_{12}$alkylsulfonyl, $C_5$-$C_{24}$arylsulfonyl or $C_6$-$C_{36}$aralkylsulfonyl groups, or $C_6$-$C_{36}$aralkyl unsubstituted or substituted by one or more hydroxy, amino, carboxyl, sulfo, $C_1$-$C_{12}$alkylsulfonyl, $C_5$-$C_{24}$arylsulfonyl or $C_6$-$C_{36}$aralkylsulfonyl groups, X and Y are, each independently of the other, mercapto, —$NR_3R_4$ or —$N^+R_3R_4R_5A^-$, wherein $R_3$, $R_4$ and $R_5$ are, each independently of the others, hydrogen or $C_1$-$C_{12}$alkyl and $A^-$ is chloride, bromide, iodide, sulfate or methylsulfate, $R_6$ and $R_7$ are, each independently of the other, hydrogen or $C_1$-$C_{12}$alkyl, and x and y are, each independently of the other, a number from 2 to 12.

$C_1$-$C_{12}$Alkyl as R or one of the radicals $R_1$-$R_5$ may be, for example, methyl, ethyl, n-propyl, isopropyl, n-butyl, isobutyl, sec-butyl, tert-butyl, n-pentyl, neopentyl, n-hexyl, n-octyl, n-decyl or n-dodecyl.

$C_6$-$C_{24}$Aryl groups as R or one of the radicals $R_1$-$R_5$ are, for example, phenyl, 3-amino-4-sulfophenyl, tolyl, mesityl, isityl, naphthyl and anthryl.

Suitable $C_6$-$C_{24}$aralkyl groups are, for example, benzyl and 2-phenylethyl.

In the method according to the invention, preference is given to the use of compounds of formula (1) wherein x and y are the same.

In preferred compounds of formula (1), x and y are 3, 4 or 6.

Preference is furthermore given to compounds of formula (1) wherein X and Y are the same.

Special preference is given to the use of compounds of formula (1) wherein R is a group of formula —NH—$(CHR_8)_z$—Z wherein $R_8$ is hydrogen or $C_1$-$C_{12}$alkyl, Z is hydroxy, mercapto or am, and z is a number from 2 to 12.

Examples of suitable compounds of the general formula (1) are the compounds of formulae (101)-(112)

(101)

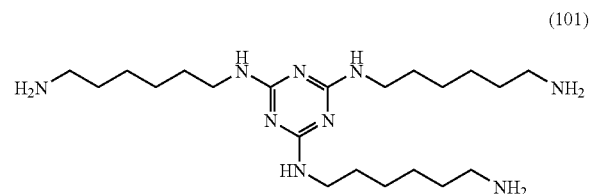

(102)

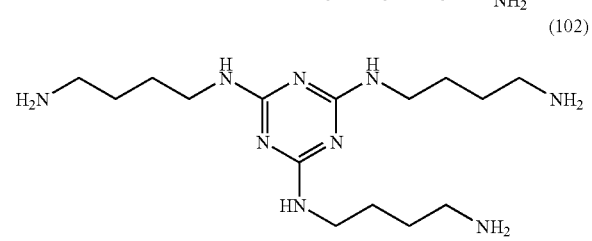

(103)

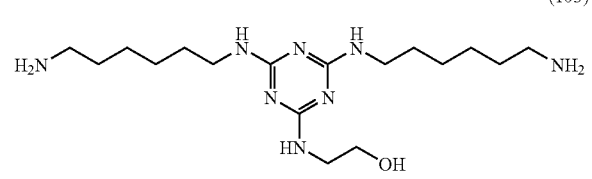

(104)

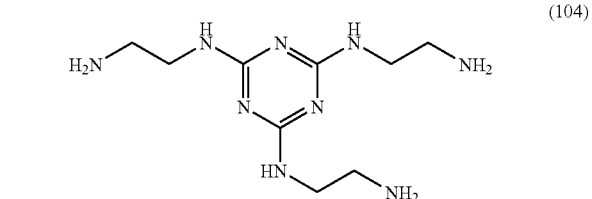

(105)

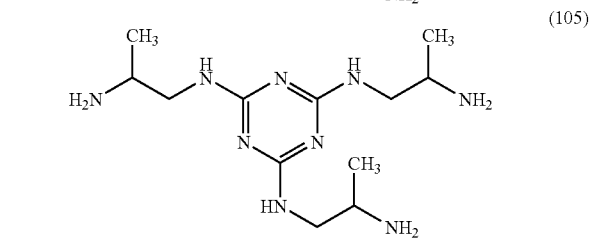

(106)

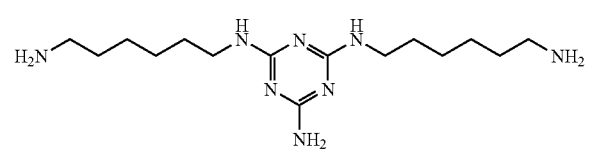

(107)

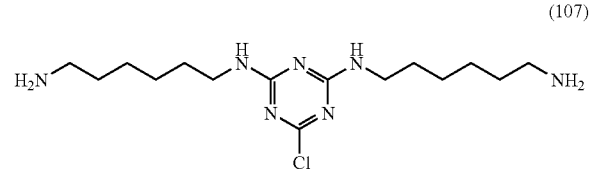

-continued

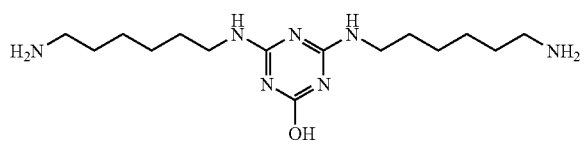
(108)

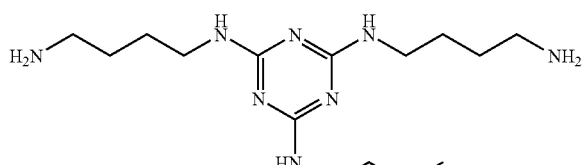
(109)

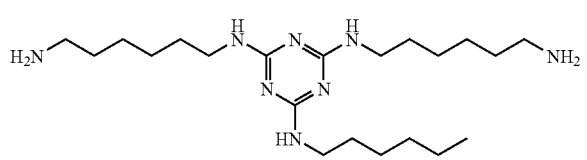
(110)

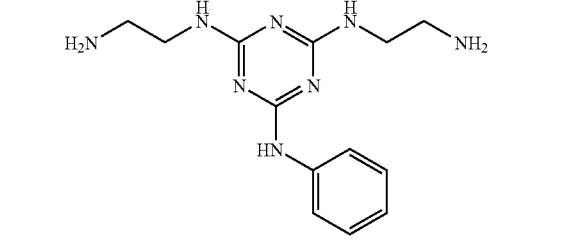
(111)

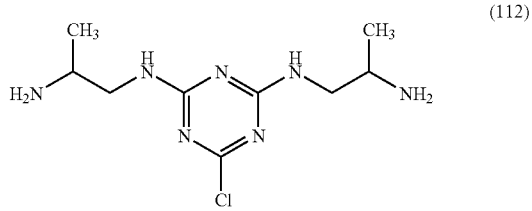
(112)

Especially preferred compounds of the general formula (1) are the compounds of formulae (101), (102), (103), (105) and (112).

The compounds of formula (1) are known or can be prepared according to known methods, for example by reacting cyanuric chloride with, in succession, a compound of formula X—(CHR$_6$)$_x$—NH$_2$, a compound of formula Y—(CHR$_7$)$_y$—NH$_2$ and a compound of formula R$_1$—NH$_2$, wherein X, Y, x, y, R$_1$, R$_6$ and R$_7$ are as defined hereinbefore.

The compounds of formula (1) used in the method according to the invention are advantageously used, irrespective of the liquor ratio, in an amount of from 0.01 to 15% by weight, preferably from 0.1 to 10% by weight and especially from 0.5 to 7% by weight, based on the weight of the polyamide fibre material.

The treatment of the polyamide fibre material with the compounds of formula (1) may be carried out after, during or, preferably, before the dyeing.

When the treatment of the polyamide fibre material with the amino-substituted triazine derivatives is carried out during the dyeing process, the method according to the invention is advantageously carried out by adding the compound of formula (1) to the dyeing liquor in the above-mentioned amount and dyeing the fibre material in the usual manner.

Preferably, however, the treatment of the polyamide fibre material with the amino-substituted triazine derivatives is carried out before the dyeing. After the pre-treatment, the textile material is advantageously rinsed with water at RT (room temperature) or slightly elevated temperature.

Suitable polyamide fibre material includes natural polyamide fibre material, e.g. wool or silk, and synthetic polyamide fibre material, e.g. polyamide-6 or polyamide-6.6, and fibre blends, e.g. wool/cellulose or polyamide/cellulose fibre blends or polyamide/wool fibre blends. The fibre material is preferably synthetic polyamide fibre material, especially microfibres.

The textile material can be used in any form, e.g. in the form of fibres, yarn, woven fabric or knitted fabric.

The treatment of the polyamide fibre material with the amino-substituted triazine derivatives is preferably carried out in accordance with the exhaust process, in which case the liquor ratio can be selected from within a wide range and is, for example, from 1:4 to 1:100, preferably from 1:5 to 1:70 and especially from 1:10 to 1:40.

Special apparatus is not required. For example, customary dyeing apparatus, e.g. open baths, winch becks, jigs, or paddle, jet or circulation apparatus, may be used.

The procedure is advantageously carried out at a temperature of, for example, from 20 to 130° C., preferably from 50 to 120° C. and especially from 60 to 100° C. The treatment time may be, for example, from 10 to 60 minutes and preferably from 15 to 40 minutes. The pH of the liquor is generally from 7 to 13, preferably from 8 to 12.5 and especially from 10 to 12.

The liquor can comprise, in addition to the adjuvant according to the invention, further customary additives, such as electrolytes, e.g. sodium chloride or sodium sulfate, dispersants and wetting agents, pH-regulators and antifoams.

The dyeings are carried out using, for example, anionic dyes or reactive dyes; any customary anionic dye or reactive dye, as described, for example, in Colour Index, 3rd edition (1971), is suitable.

Examples of anionic dyes include sulfo-group-containing monoazo, polyazo, metal complex azo, anthraquinone, phthalocyanine and formazan dyes.

The anionic dyes used in dyeing the polyamide fibre material are either in the form of their free sulfonic acids or, preferably, in the form of their salts.

The dyes used in dyeing the polyamide fibre material may comprise further additives, e.g. sodium chloride or dextrin.

Dyeing of the polyamide fibre material can be carried out in accordance with customary dyeing or printing methods, for example in accordance with the padding or exhaust process. The dye liquors or printing pastes may comprise, in addition to water and the dyes, further additives, for example wetting agents, antifoams, levelling agents or agents that influence the characteristics of the textile material, for example softeners, flame-retardants, or dirt-, water- and oil-repellents, and also water-softeners and natural or synthetic thickeners, for example alginates and cellulose ethers.

The amounts in which dyes are used in the dye baths can vary within wide limits depending on the required depth of shade; in general, amounts of from 0.01 to 15% by weight, especially from 0.01 to 10% by weight, based on the material to be dyed, have proved to be advantageous.

The dyeing with anionic dyes or reactive dyes is preferably carried out at a pH of from 1 to 8 and especially from 2 to 7. The liquor ratio can be selected from within a wide range, for example from 1:3 to 1:50, preferably from 1:5 to 1:30. Dyeing is preferably carried out at from 50 to 130° C. and especially from 80 to 120° C.

Following the method according to the invention there are obtained dyeings of dyes, e.g. anionic dyes or reactive dyes, on polyamide fibre material, which dyeings exhibit a substantial improvement in terms of the depth of shade, without the fastness-to-washing or fastness-to-light properties being adversely affected.

The invention relates also to a textile adjuvant comprising an aqueous solution of a compound of formula (1).

The textile adjuvants according to the invention may comprise, as further additives, for example wetting agents, dispersants or pH-regulators.

The Examples that follow serve to illustrate the invention. The temperatures are given in degrees Celsius, parts are parts by weight, and percentages refer to percentages by weight, unless otherwise specified. Parts by weight relate to parts by volume in the same ratio as kilograms to litres.

I. Preparation Examples

I.1. Compound of Formula (101)

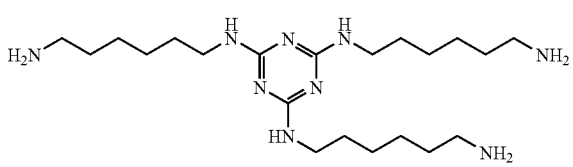

9.22 g of cyanuric chloride, 35 g of cold water, 50 g of ice, 0.5 g of disodium phosphate and 1 drop of Irgapadol FFU (dispersant, Ciba Specialty Chemicals) are introduced into a 750 ml sulfonating flask and stirred for 30 minutes at 0-2° C. There is then added a solution (neutralised to pH 7.5 at 2-5° C. using 4N HCl) of 17.6 g of 1,6-diaminohexane and 35 g of water. The mixture is stirred at 2° C. for 3 hours, the pH being held constant at 7.0 by the addition of 1N NaOH. The temperature is then increased slowly to 25° C.; the pH is still held constant at 7.0. After stirring for 3 hours at 25° C., the temperature is increased very slowly and in steps to 95° C., at pH 7.0. After stirring for 2 hours at 95° C., the reaction is complete. The batch is cooled and the by-products are filtered off.

405 g of a clear, colourless solution having an active content of 4.5% are obtained.

I.2. Compound of Formula (102)

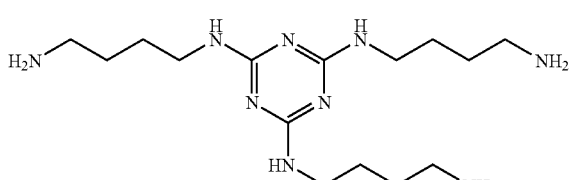

Analogously to Example I.1, 9.22 g of cyanuric chloride are reacted with 13.4 g of 1,4-diaminobutane. 505 g of a clear, colourless solution having an active content of 4.1% are obtained.

I.3. Compound of Formula (103)

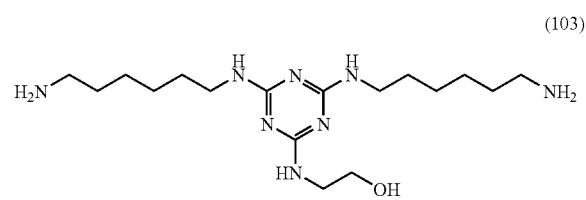

4.61 g of cyanuric chloride, 25 g of cold water, 30 g of ice and 1 drop of Irgapadol FFU (dispersant, Ciba Specialty Chemicals) are introduced into a 350 ml sulfonating flask and stirred for 30 minutes at 0-2° C. A solution of 1.53 g of ethanolamine and 5.0 g of water is added dropwise over 40 minutes. During the addition, the pH is held constant at 7.0 to 7.5. After the addition, the mixture is stirred at 2° C. for 90 minutes, the pH being held constant at 7.0 by the addition of 1N NaOH. There is then added a solution (neutralised to pH 7.5 at 2-5° C. using 4N HCl) of 5.8 g of 1,6-diaminohexane and 10 g of water. The temperature is then increased very slowly to 50° C., the pH being held constant at 7.0. The mixture is stirred for 2 hours at 50° C. The temperature is then increased very slowly and in steps to 95° C., at pH 7.0. After 4 hours at 95° C., the reaction is complete. The batch is cooled and the by-products are filtered off.

182 g of a clear, colourless solution having an active content of 2.9% are obtained.

I.4. Compound of Formula (112)

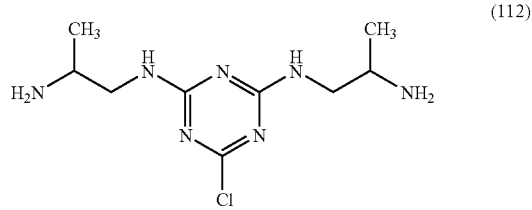

18.4 g of cyanuric chloride, 30 g of cold water, 30 g of ice and 1 drop of Irgapadol FFU are introduced into a 350 ml sulfonating flask and stirred for 30 minutes at 0-2° C. There is then added a solution (neutralised to pH 7.5 at 2-5° C. using 37% HCl) of 7.45 g of 1,2-diaminopropane and 20 g of water. The mixture is stirred at 2° C., the pH being held constant at 6.5 by the addition of a solution of 7.45 g of 1,2-diaminopropane and 8.0 g of water. After the addition is complete, stirring is carried out at 2° C. for a further one hour, the pH being maintained at 6.5 by the addition of 4N NaOH. The temperature is then increased slowly to 25° C., the pH still being held constant at 6.5. After 2 hours at 25° C., the reaction is complete. The by-products are filtered off.

195 g of a clear, colourless solution having an active content of 16% are obtained.

II. Application Examples

II.1. Pretreatment and Dyeing of Microfibres (a) Pretreatment 5 g of polyamide microfibre fabric (PA-Meryl microfibre 5-3101) are immersed, at RT (room temperature), in a liquor containing 5.55 g of the product of Preparation Example I.1 (5% of active product, based on the fibre weight) and 45 g of water, adjusted to pH 11 using NaOH. The liquor is then heated to 98° C. at a heating rate of 2° C./minute. After 30 minutes at 98° C., the liquor is cooled to 60° C. at 3° C./minute.

After the pretreatment, the fabric is rinsed with water, first at 25° C. and then at 50-60° C., and subsequently with dilute acetic acid (pH 6.0) at 25° C.

(b) Dyeing

The pretreated fabric is immersed in a liquor adjusted to pH 3 using 80% acetic acid and containing 8% Eriofast Red 2B (Ciba Specialty Chemicals) and 1 g/litre of Tinovetin JUN (wetting agent, Ciba Specialty Chemicals), at RT. The liquor is then heated to 98° C. at a heating rate of 2° C./minute. After 60 minutes at 98° C., the liquor is cooled to 60° C. at 3° C./minute.

After the dyeing, the fabric is rinsed first at 50° C. with water, then for 20 minutes at 70° C. with aqueous $Na_2CO_3$ solution, at 30-40° C. with water and finally at RT with dilute acetic acid (0.5 ml of 80% acetic acid per litre) and again with water.

II.2. Example II.1. is repeated using 3.4 g of the product of Preparation Example I.1.

II.3. Example II.1. is repeated using 6.1 g of the product of Preparation Example I.2.

II.4. Example II.1. is repeated using 8.7 g of the product of Preparation Example I.3.

II.5. Example II.1. is repeated using 1.6 g of the product of Preparation Example I.4.

Dyeings having dark shades are obtained, without the fastness to washing and fastness to light being adversely affected.

What is claimed is:

1. A method of increasing the depth of shade of dyed natural or synthetic polyamide fibre materials, which comprises treating the fibre material before, during or after dyeing with a liquor comprising a compound of formula (1)

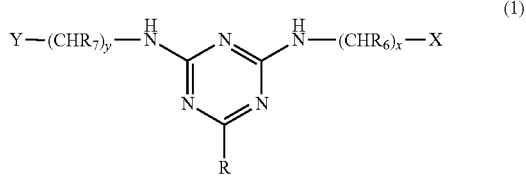

(1)

wherein R is halogen, $C_1$-$C_{12}$ alkyl, $C_5$-$C_{24}$ aryl, $C_6$-$C_{36}$ aralkyl, —$OR_1$ or —$NR_1R_2$, $R_1$; and $R_2$ being, each independently of the other, hydrogen, $C_1$-$C_{12}$ alkyl unsubstituted or substituted by one or more hydroxy, amino, mercapto, carboxyl, sulfo, $C_1$-$C_{12}$ alkylsulfonyl, $C_5$-$C_{24}$ arylsulfonyl or $C_6$-$C_{36}$ aralkylsulfonyl groups, $C_5$-$C_{24}$ aryl unsubstituted or substituted by one or more hydroxy, amino, carboxyl, sulfo, $C_1$-$C_{12}$ alkylsulfonyl, $C_5$-$C_{24}$ arylsulfonyl or $C_6$-$C_{36}$ aralkylsulfonyl groups, or $C_6$-$C_{36}$ aralkyl unsubstituted or substituted by one or more hydroxy, amino, carboxyl, sulfa, $C_1$-$C_{12}$ alkylsulfonyl, $C_5$-$C_{24}$ arylsulfonyl or $C_6$-$C_{36}$ aralkylsulfonyl groups;

X and Y are, each independently of the other, mercapto, or —$NR_3R_4$, wherein $R_3$ and $R_4$ are, each independently of the other, hydrogen or $C_1$-$C_{12}$alkyl;

$R_6$ and $R_7$ are, each independently of the other, hydrogen or $C_1$-$C_{12}$ alkyl;

and x and y are, each independently of the other, a number from 2 to 12.

2. A method according to claim 1, which comprises using a compound of formula (1) wherein x and y are the same.

3. A method according to claim 1, which comprises using a compound of formula (1) wherein x and y are 3, 4 or 6.

4. A method according to claim 1, which comprises using a compound of formula (1) wherein X and Y are the same.

5. A method according to claim 1, which comprises using a compound of formula (1) wherein R is a group of formula —NH—$(CHR_8)_z$—Z wherein $R_8$ is hydrogen or $C_1$-$C_{12}$ alkyl, Z is hydroxy, mercapto or amino, and z is a number from 2 to 12.

6. A method according to claim 1, wherein the compound of formula (1) is present in the liquor in an amount of from 0.01 to 15% by weight, based on the weight of the polyamide fibre material.

7. A method according to claim 1, wherein the fibre material is treated before the dyeing.

8. A method according to claim 1, wherein the treatment with the liquor comprising the compound of formula (1) is carried out at a temperature of from 20 to 130° C.

9. A method according to claim 7, wherein the pretreatment is carried out at a pH of from 7 to 13.

10. A method according to claim 1, wherein the treatment with the liquor comprising the compound of formula (1) is carried out in accordance with the exhaust process.

11. A method according to claim 1, wherein the polyamide fibre material is in the form of microfibres.

12. A textile adjuvant comprising an aqueous solution of a compound of formula (1) according to claim 1.

* * * * *